US00PP17198P3

(12) United States Plant Patent
Hanes

(10) Patent No.: US PP17,198 P3
(45) Date of Patent: Nov. 7, 2006

(54) *PETUNIA* PLANT NAMED 'JAM LAVERTWO'

(50) Latin Name: *Petunia hybrida*
Varietal Denomination: Jam Lavertwo

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 29 days.

(21) Appl. No.: 11/094,746

(22) Filed: Mar. 31, 2005

(65) Prior Publication Data

US 2006/0225175 P1 Oct. 5, 2006

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP13,539 P2 * 2/2003 Sakazaki ..... Plt./356
PP14,007 P2 * 7/2003 Bessho ..... Plt./356
PP15,655 P2 * 3/2005 Hanes ..... Plt./356

OTHER PUBLICATIONS

UPOV ROM CTITM Computer Database GTI Jouve Retrieval Software 2005/04 citation for 'Jam Lavertwo'.*
Anonymous—Canadian Ornamental Plant Foundation 'Jam Lavertwo' available at http://copf.org/plant.asp?PIN=4377.*

* cited by examiner

*Primary Examiner*—Wendy Haas
(74) *Attorney, Agent, or Firm*—Jondle & Associates P.C.

(57) ABSTRACT

A *petunia* cultivar particularly distinguished by its large, light lavender flowers, early flowering and large leaf size is disclosed.

1 Drawing Sheet

Figure 1:
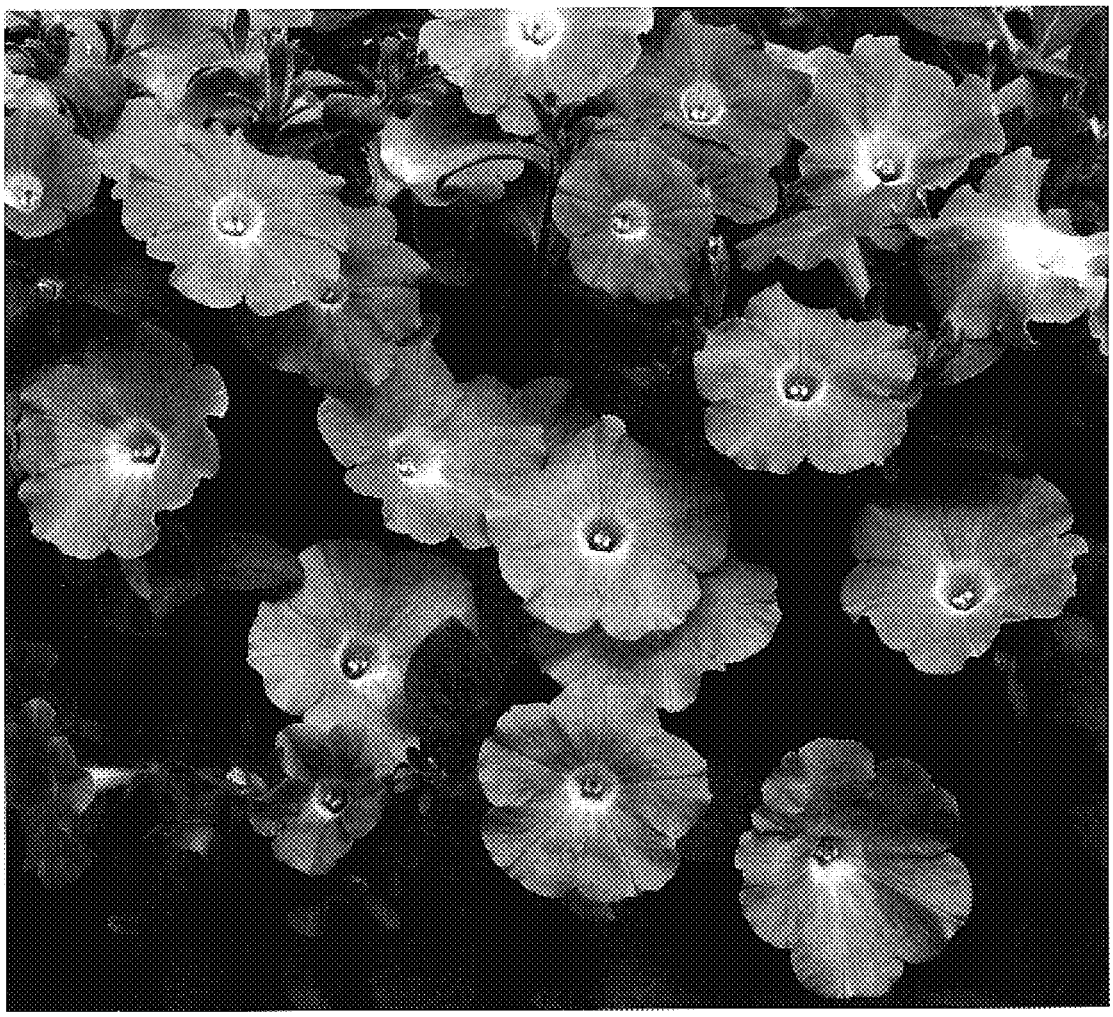

Genus and species: *Petunia hybrida.*
Variety denomination: 'Jam Lavertwo'.

BACKGROUND OF THE NEW PLANT

The present invention comprises a new and distinct cultivar of *petunia*, botanically known as *Petunia hybrida*, and hereinafter referred to by the cultivar name 'Jam Lavertwo'. The new cultivar originated from a hybridization made in the year 2001 in Gilroy, Calif. The female parent was 'Suncatcher Lavender' (U.S. Plant Pat. No. 14,007), while the male parent was 'Jamboree Light Blue' (U.S. Plant Pat. No. 15,655).

The new cultivar was created in 2001 in Gilroy, Calif. and has been asexually reproduced repeatedly by vegetative cuttings and tissue culture in Gilroy, Calif. and Andijk, The Netherlands over a two-and-a-half-year period. The plant has also been trialed at Gilroy, Calif., Litchfield, Mich. and Andijk, The Netherlands. The present invention has been found to retain its distinctive characteristics through successive asexual propagations.

DESCRIPTION OF PHOTOGRAPH

This new *petunia* plant is illustrated by the accompanying photograph which shows blooms, buds, and foliage of the plant in full color; the colors shown are as true as can be reasonably obtained by conventional photographic procedures. The photograph is of a four-month-old plant grown in a lexan-covered greenhouse in a spring trial setting.

FIG. 1. The photograph shows blooms, buds and foliage.

DESCRIPTION OF THE NEW CULTIVAR

The following detailed descriptions set forth the distinctive characteristics of 'Jam Lavertwo'. The data which define these characteristics were collected from asexual reproductions carried out in Gilroy, Calif. The plant history was taken on four-month-old plants grown in one-gallon pots in a poly-covered greenhouse. Color readings were taken in the greenhouse in the late winter season under natural light. Color references are primarily to The R.H.S. Colour Chart of The Royal Horticultural Society of London (R.H.S.) (2001 edition). Texture description details were observed under a dissecting microscope.

DETAILED BOTANICAL DESCRIPTION

Classification:
*Botanical.—Petunia hybrida.*
*Common name.—Petunia.*

Growth:
*Growth and branching habit.*—Good vigorous habit, well-branched.
*Form.*—Semi upright and decumbent.
*Height.*—15.0–20.0 cm as measured from soil level, excluding blooms.
*Width.*—30.0–35.0 cm excluding flowers.
*Time to produce a finished flowering plant.*—8–11 weeks for a 4–6 inch pot.
*Outdoor plant performance.*—Does well in full sun; used as a hanging plant, in mixed containers, patio containers.
*Time to initiate roots.*—18–23 days.
*Root description.*—White, fibrous.

Leaves:

*Arrangement.*—Alternate; upper leaves subalternate.

*Immature leaf.*—Color: Upper surface: RHS 137C. Lower surface: Between RHS 138A and RHS 138B. Length: 2.5–5.0 cm. Width: 1.5–2.5 cm.

*Mature leaf.*—Color: Upper surface: RHS 137C. Lower surface: Closest to RHS 138A. Length: 5.5–5.6 cm. Width: 2.8–4.1 cm. Shape: Elliptical to obovate. Margin: Entire. Apex: Rounded. Base: Acuminate. Texture: Hirsute, few glandular hairs. Venation: Palmate. Venation color: RHS 144B.

*Petioles.*—Length: 0.2–0.3 cm. Width: 0.3 cm. Color: RHS 144B. Texture: Hirsute, few glandular hairs.

Stems:

*Length.*—25.0–30.0 cm.

*Diameter.*—0.3 cm.

*Internode length.*—1.5–3.0 cm.

*Color.*—RHS 144B.

*Texture.*—Hirsute, few glandular hairs.

*Stem anthocyanin.*—None.

*Pedicel.*—Color: Between RHS 144A and RHS 144B. Length: 1.7–2.0 cm. Diameter: 0.1 cm. Texture: Hirsute, few glandular hairs.

Flower buds:

*Shape.*—Oblong.

*Diameter.*—0.4–0.5 cm.

*Length.*—3.0–3.5 cm.

*Color when bud is first starting to open.*—RHS N82C.

Inflorescence:

*Blooming habit.*—Continuous throughout the growing season; good floriferousness.

*Lastingness of individual blooms.*—4–8 days.

*Fragrance.*—None.

*Inflorescence type.*—Flowers solitary in upper leaf axis.

*Floret type.*—Funnelform; 5 lobed petals, fused at base.

Flowers:

*Immature flower.*—Color: Upper side: Between RHS N80A and RHS N80B. Underside: Between RHS 76B and RHS 76C. Color of main veins: RHS 144B. Flower diameter: 3.5–5.0 cm.

*Mature flower.*—Color: Upper side: Between RHS N81D and RHS 77B. Color of main veins: Faint RHS 145B. Color of secondary veins: Faint RHS 77B. Underside: RHS 69D. Color of main veins: RHS 144B. Flower diameter: 5.5–5.8 cm.

*Corolla.*—Tube color inside: RHS 4D. Color of veins: RHS 145C. Tube length: 2.0–2.5 cm. Texture: Hirsute and glandular hairs.

*Petals.*—Apex: Obtuse. Base: Fused. Margin: Entire. Waviness: Weak. Lobation: Moderate. Texture: Papillose.

*Calyx.*—5-lobed.

*Sepals.*—Number: 5, deeply lobed, fused at base. Color: RHS 137B. Length: 1.2–1.4 cm. Width: 0.3–0.5 cm. Shape: Oblong. Apex: Rounded. Texture: Short glandular hairs.

Reproductive organs:

*Stamens.*—Number: 5; 2 taller and 3 shorter. Filament color: RHS N155D. Filament length: 1.5–1.9 cm. Pollen color: RHS 8D.

*Pistil.*—Number: 1. Length: 1.9 cm. Stigma color: RHS 144B. Style color: RHS 145C.

*Fruit/seed set.*—Not observed.

Disease and insect resistance: Not observed.

COMPARISON WITH KNOWN CULTIVARS

'Jam Lavertwo' differs from the female parent 'Suncatcher Lavender' (U.S. Plant Pat. No. 14,007) by having more flowering in the center of the plant and by not being as sensitive to leaf burning in high light as 'Suncatcher Lavender'. In addition, 'Jam Lavertwo' has a larger leaf size and a lighter lavender flower with more prominent veins than 'Suncatcher Lavender'.

'Jam Lavertwo' differs from the male parent 'Jamboree Light Blue' (U.S. Plant Pat. No. 15,655) by having a larger leaf size, lighter lavender flower color and by being earlier to flower than 'Jamboree Light Blue'.

I claim:

1. A new and distinct *petunia* plant as shown and described herein.

* * * * *